United States Patent [19]

Williams et al.

[11] Patent Number: 5,107,064
[45] Date of Patent: Apr. 21, 1992

[54] FAST-CYCLING DWARF *BASSICA OLERACEA*

[75] Inventors: Paul H. Williams; Alex W. May, both of Madison, Wis.

[73] Assignee: Wisconsin Alumni Research Foundation, Madison, Wis.

[21] Appl. No.: 111,421

[22] Filed: Oct. 22, 1987

[51] Int. Cl.$^5$ ................................................ A01H 5/00
[52] U.S. Cl. ............................ 800/230; 800/DIG. 15; 800/DIG. 16
[58] Field of Search .................. 800/1; 47/DIG. 1, 58

[56] References Cited

U.S. PATENT DOCUMENTS

| | | | |
|---|---|---|---|
| 4,098,021 | 7/1978 | Gruber | 47/58 |
| 4,143,486 | 3/1979 | Maan | 47/58 |
| 4,378,655 | 4/1983 | Johnson | . |
| 4,499,687 | 2/1985 | Lawrence, Jr. et al. | . |

OTHER PUBLICATIONS

Polacco, M. et al. (1987), Nuclear Genes That Alter . . . Developmental Genetics 8:389-403.
Ghosh, P. et al. (1979), Embryo Culture as a Method . . . Proc. Indian Natl. Sci. Acad., Part B 45(6), 605-612.
*Science*, vol. 232, pp. 1385-1389, Rapid-Cycling Populations of Brassica, Williams and Hill.
*Touchstone*, vol. 19, No. 2, pp. 2-5, Life in the Fast Lane, Paul L. du Breuil.
*CrGC Resource Book*, 1985, Paul H. Williams.
Ross et al. (1987), Ann. Bot. 59:107-110, abstracted May 15, 1987.

*Primary Examiner*—Elizabeth C. Weimar
*Assistant Examiner*—Che S. Chereskin
*Attorney, Agent, or Firm*—Quarles & Brady

[57] ABSTRACT

This invention relates to a novel dwarf *Brassica oleracea* plant and a useful variety of rapid-cycling *B. oleracea* containing the single recessive mutant gene for the dwarf phenotype homozygously. The single gene (dwfl) is produced by mutagenesis and selection and is useful for producing novel types and varieties of dwarf Brassica plants for ornamental or agricultural purposes.

8 Claims, 2 Drawing Sheets

FAST-CYCLING DWARF *BASSICA OLERACEA*

This invention was made with U.S. government support awarded by the USDA (Hatch funds). The U.S. Government has certain rights in this invention.

FIELD OF THE INVENTION

The present invention relates to a rapid-cycling variety of *Brassica oleracea* which has been genetically altered to have a reduced internode length. In addition, the present invention is directed to a rapid-cycling dwarf *Brassica oleracea* plant and a single recessive gene in the plant which can be transferred to other *Brassica oleracea* varieties. The variety of the present invention is immediately useful as an educational tool for experiments involving the use of fast-cycling dwarf *Brassica oleracea* plants.

BACKGROUND OF THE INVENTION

*Brassica oleracea* is a species within the genus Brassica in the family of plants known as Cruciferae. Plants of this family are familiarly referred to as Crucifers because of the four-petalled flowers which resemble a cross or crucifix. The Crucifer family is so large that it is broken into sub-groups, referred to as genera. One of the genera of the Crucifer family is the Brassica genus.

*Brassica oleracea* is a species with a wide range of diverse morphotypes, including cabbage, cauliflower, broccoli, brussel sprouts, kohlrabi, collards, and various kales, commonly known as the cole crops. All of these forms, with the exception of some broccolis, a few cauliflower types, and Chinese kale require a period of cool temperature, i.e., 35°-40° F. for approximately 2-12 weeks, in order to induce the plant from the vegetative to the flowering stage. Under normal seed production of the cole crops, seeds are sown in July or August in regions with a cool, mild winter, such as the Pacific coast of North America, Northern Europe, or Japan. The crop grows into the fall and winter where it undergoes vernalization. As used here, the term "vernalization" means the inducement of flowering by subjecting a growing crop to a low temperature, i.e., about 5° C. The crop flowers in the late spring. Seeds are normally ripe and harvested in August. The entire seed-to-seed life cycle, hereinafter referred to as "life cycle", of the crop takes a little more than one year.

It is well known that the above-listed vegetables are excellent nutrition sources, forming an essential part of the diets of many nations. Additionally, it has recently been discovered that varieties of several Brassica species make excellent resource tools, as the plant may be used as a repository for many genetic mutations of scientific, educational and potential economic interests. Reference is made to Williams, Paul H. and Curtis B. Hill, "Rapid-Cycling Populations of Brassica", *Science*, Vol. 232, pp. 1385-1389 (Jun. 13, 1986).

The cultivated Brassicas include six interrelated species, three of which (*B. nigra, B. campestris,* and *B. oleracea*) and the other three of which are diploids (*B. juncea, B. napus,* and *B. carinata*) are amphidiploid derivatives of the diploid species. Stocks of all these species, and the related species of radish, *Raphanus sativus*, are established, maintained and made available by the Crucifer Genetics Cooperative, Dept. of Plant Pathology, 1630 Linden Drive, Madison, Wis. 53706. Under conventional taxonomy, the three diploid species are assigned genomic descriptors as are their amphidiploid derivatives, with the cytoplasmic genome written in upper case corresponding to the lower case nuclear genome of the species contributing the cytoplasm, i.e. *B. campestris* ($n=10$) is Aaa, *B. nigra* ($n=8$) is Bbb, *B. oleracea* ($n=9$) is Ccc, *B. juncea* ($n=18$) is ABaabb, *B. carinata* ($n=17$) is BCbbcc, *B. napus* ($n=19$) is ACaacc, and *R. sativus* ($n=9$) is Rrr. The cytogenetic interrelationships of the six Brassica species have been documented for many years. Morinaga, "Interspecific Hybridization in Brassica VI. The Cytology of $F_1$ hybrids of *B. juncea* and *B. nigra*," *Cytology*, 6, pp. 62-67 (1934). Since that time numerous studies have demonstrated the feasibility of the interspecific transfer of genes among the various Brassica species. Yarnell, "Cytogenetics of the Vegetable Crop. II. Crucifers." *Bot. Rev.*, 22, pp. 81-166 (1956), McNaughton et al., "Interspecific and Intergeneric Hybridization of the Brassicae with Special Emphasis on the Improvement of Forage Crop," Scottish Plant Br. Sta. 57th Am. Rept. Invergowrie, pp. 75-100 (1978). Thus it is possible, under current technology and using conventional plant breeding techniques, to move genetic traits both within a species and between species in the Brassica genus.

The three diploid species of Brassica, including *B. oleracea*, are insect pollinated and strongly out-breeding with self incompatibility controlled by a multiple allelic series of genes. The selfing of incompatible plants can, however, be accomplished by bud pollination or by the placement of "self" pollen on the immature stigmas of the plant one to two days prior to anthesis.

Detailed information about Crucifer stocks, husbandry and cultivation, and genetics as well as specific techniques, such as manual pollination, can be found in the Resource Book of the Crucifer Genetics Cooperative and available from it. One of the stocks available from the Crucifer Genetics Cooperative, and available from it, is a population of *Brassica oleracea* plants referred to as CrGC-3. This is a fast-cycling population of plants, with a mean flower time of 30 days and averaging 23 cm in height. The plants in this population are fully fertile and are now used by plant breeders and researchers in many applications of basic and applied science.

SUMMARY OF THE INVENTION

Accordingly, it is an object of the invention to develop a base variety of fast-cycling *Brassica oleracea* for research purposes and to create a model plant in this species for use in education. It is also an object to develop a shorter, more manageable plant with substantially reduced internode length so that the plants would grow in a more compact form. It is also an object to produce such a plant which will readily adapt to the environment of a research laboratory.

These objects and others are met by the present invention which is directed to a method for producing a rapid cycling or fast growing, dwarf *Brassica oleracea* plant. The genetic factor capable of transmitting the shortened internode characteristics to the dwarf *Brassica oleracea* plants has been determined to be a single recessive gene designated dwf1. It is a feature of the present invention that this single gene may be used in and transferred among the various *B. oleracea* varieties, and to other Brassica species.

The present invention is also directed to a method of producing seeds for fast growing, dwarf *Brassica oleracea* plants, which upon growth yield dwarf *Brassica oleracea* plant having reduced internode length.

The resulting plant will be shorter and more manageable with substantially reduced internode length, so that the plants will grow in a more compact form. The seed-to-seed life cycle of the dwarf *Brassica oleracea* plant is also shortened in order to enhance its application to the fields of science and education. The plant may be used as a repository for many genetic mutations of scientific, educational and potential economic interest. Because the fast growing dwarf plant may be conveniently grown under standard research conditions, it may become the stock plant of choice in the development of other mutant stocks for educational purposes.

Further, the resulting plant may have other commercially interesting uses of culinary, ornamental, and economic value.

Other objects, advantages and features of the present invention will become apparent from the following drawings and specification.

DETAILED DESCRIPTION OF THE INVENTION

Figure 1:
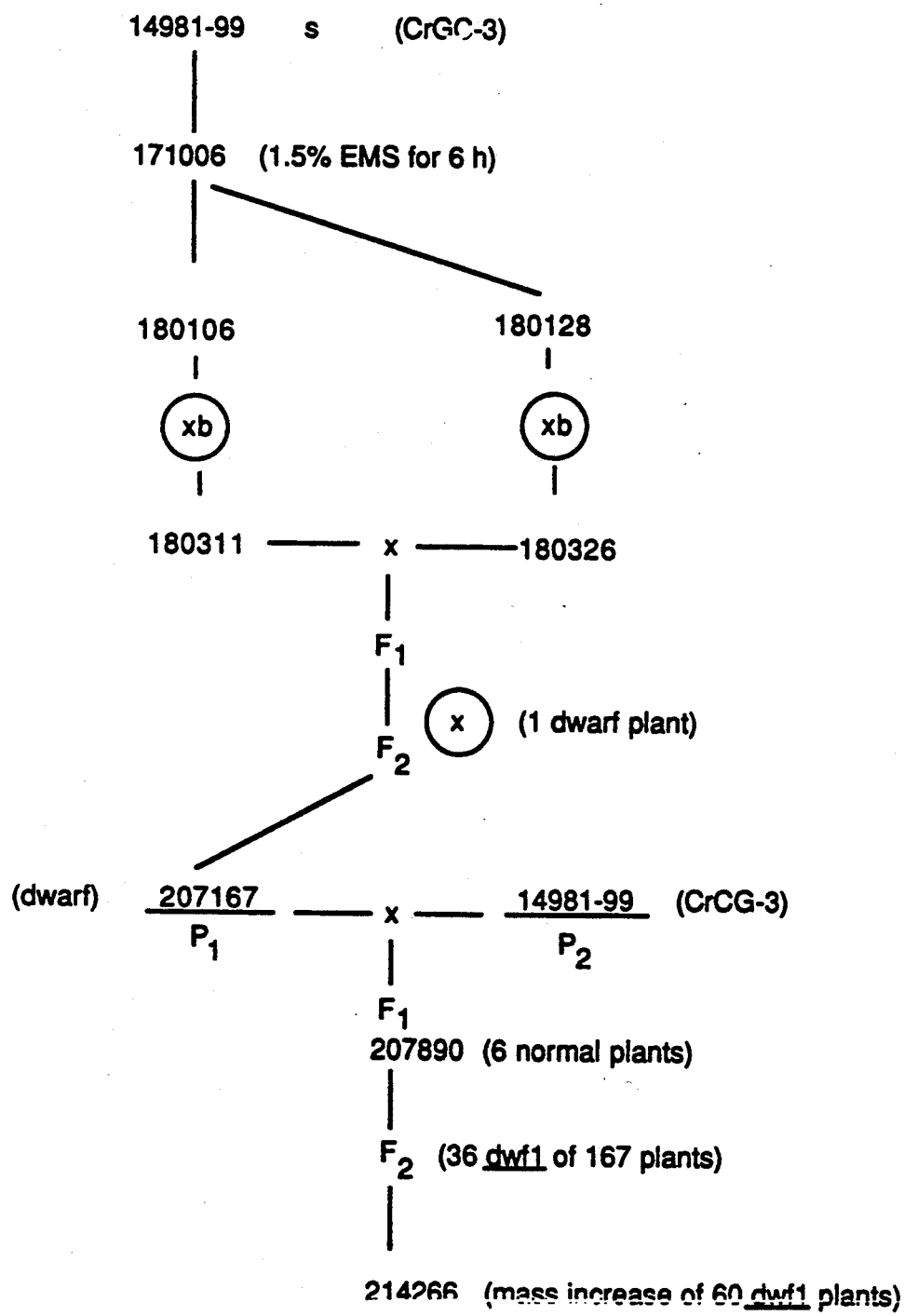
FIG. 1 is a diagrammatic view of a procedure used by the applicant to produce a dwarf-type *Brassica oleracea* variety.

The present invention is directed to developing unique dwarf plants of the species *Brassica oleracea* having useful characteristics for laboratory, classroom, horticultural as well as agricultural use. Although there may be several methods which may be used to develop this invention, selection under the desired criteria and mutation and selection were used as the most efficient and economical method for introducing desirable dwarf characteristics into a line of Brassica plants.

As the term is used herein, dwarfism is a condition wherein all plant parts are either normal size or fully functional but wherein the plant is significantly reduced in size by a significant reduction or shortening of the internode length of the plant. This reduction in internode length should not interfere with the reproductive ability or productivity of the plant. The creation of the recessive dwarf trait disclosed here was accomplished in plants of the population CrGC-3, a fast-cycling population of *B. oleracea*. Plants of CrGC-3 have a typical internode length of 30 mm. Plants of CrGC-3 having the dwarf trait, as disclosed hereinafter, have an internode length of 1-2 mm. Since dwarfism is sometimes defined to be a reduction of at least 35%, this trait conditions a strongly dwarf phenotype.

Because the dwarf trait described here was first created in plants of CrGC-3, the creation of that stock will be described here first to enable others to create similar stocks. Then the creation of the dwarf trait in these plants will be discussed.

Development of the Rapid-Cycling Base Population of *Brassica oleracea* (CrGC-3)

It was desired to speed up the life cycle of the cole crops for research purposes and to create a model plant for use in education and research. A fast-cycling plant population was considered desirable in order to speed the development of research in Brassica genetics and to enable useful traits to be introduced much more quickly and efficiently into Brassica varieties of commercial agricultural interest. A fast-flowering *Brassica oleracea*, which required no cool vernalization and which could produce a flowering and seed producing reproductive plant under a standardized set of conditions, was determined as an objective. To reach that objective, a standardized set of desirable conditions for the population to be created was developed. Suitable plants were then identified and cross-bred to create heterogeneous hybrid progeny which were selected for best performance under the standard conditions. The standardized conditions for selection of rapid cycling *Brassica oleracea* are set forth in Table 1 as follows:

TABLE 1

GROWTH CRITERIA

| | |
|---|---|
| 1. | A 24 hour photoperiod of 200-250 u Einsteins per second per meter square of irradiance in the PAR (photosynthetically active region) of the electromagnetic spectrum under cool white fluorescent bulbs. |
| 2. | Growth in a standard growing medium of 1 part fine horticultural vermiculite and 1 part sphagnum moss peat, finely screened (commercially available as Jiffy Mix), generically known as peat-lite. |
| 3. | Temperature between 22 and 26° C. continuously. |
| 4. | Nutrient solution irrigated with one-half strength Hoagland's Solution*. Plants were watered daily (soak soil to runoff). |
| 5. | Plants grown in plastic multipot trays having a container size 4 × 3 × 5 cm. with a soil volume of 60 cubic centimeters of growth medium per pot. |

*Hoagland's Solution Used to Irrigate Crucifers
To prepare half strength Hoagland's solution, dispense the amounts below in 2 liters of water.
Mixture (use 2.0 ml per liter water)
1.0M KNO$_3$ (Potassium Nitrate) = 1820 grams
0.2M KH$_2$PO$_4$ (Potassium Phosphate monobasic) = 491 grams
0.4M MgSO$_4$7H$_2$O (Magnesium Sulphate) = 1775 grams (or 866.83 grams anhydrous)
—distilled water to 18 liters stock solution
Calcium Nitrate (use 2.5 ml per liter water)
1.25M CaNO$_3$ = 5313.6 grams
—distilled water to 18 liters stock solution
A-Z (micronutrients) (use 2.0 ml per liter water)
28.6 grams H$_3$BO$_3$ (Boric Acid)
18.1 grams MnCl$_2$4H$_2$O (Manganese Chloride)
2.2 grams ZnSO$_4$7H$_2$O (Zinc Sulfate)
0.8 grams CuSO$_4$5H$_2$O (Copper Sulfate)
0.9 grams H$_2$MoO$_4$H$_2$O (Molybdic Acid)
—distilled water to 1 liter; then use 450 ml/18 liters
Iron (use 2.0 ml per liter water)
25.02 grams FeSO$_4$7H$_2$O
33.48 grams Na EDTA (ethylene diamine tetraacetic acid)
—Dissolve in 2 liters H$_2$O by heating to 80° C. for one hour. Let cool slightly and add water to total volume of 18 liters.

To begin the development of a fast-cycling population, existing plants of *B. oleracea* closest to the defined criteria were identified. From stocks of tropical cauliflower (*oleracea* var botrytis) cultivars Tropical Days, Exhibition, Snow Queen, and Chinese kale (*oleracea* var alboglabra), collected in Taiwan and China, several plants were found which would reproduce under the conditions specified in Table 1. These plants were inter-pollinated to produce a crop of seed. The seed was sown and used as the beginning population of a breeding program in which recurrent mass selection was followed using the criteria listed in Table 2 as follows:

TABLE 2

Selection Criteria

1. Minimum time to flower from sowing.
2. Ability to produce viable seed within 30 days of the last pollination on the plant.

3. Ability to produce a good set of seed (10-20 seeds) for each flower pollinated.
4. Ability to grow under the environmental conditions given in Table 1.
5. Production of plants that were not excessively leafy or tall. Most plants were between 45 and 60 cm. tall.
6. Production of seed that would germinate immediately upon sowing and that lacked the trait of seed dormancy.
7. A selection intensity of 10% was exercised on each population at each generation of recurrent selection; that is, the first 10% of the plants that flowered in a given population were interpollinated to produce seed for the next generation. Generation sizes were a minimum of 300 plants. Thus, approximately 30 or more plants were selected to produce each new generation.
8. Recurrent selection was discontinued when 50% of the plants in a generation flowered within a 2-day period. This provided a high degree of uniformity within the population with respect to flowering time, and ensured that the population was sufficiently homogeneous with respect to flowering that it could be conveniently pollinated over a 4 or 5 day period and be expected to contain representative genetic information from greater than 95% of the individuals in the population.

When recurrent selection was stopped, the population was designated CrGC-3and further designated as the base population (BP) of the rapid cycling (RC) *Brassica oleracea*. This seed is described in Williams, Paul H. and Curtis B. Hill (supra). A pedigree or genealogy of the CrGC-3 population is given in Table 3 as follows:

TABLE 3

PEDIGREE OF THE RAPID-CYCLING BASE POPULATION OF *BRASSICA OLERACEA*, CrGC-3a

| Generation | Plant Numbers | Comments and days to first flower |
|---|---|---|
| M1 | 93001-93021 | 20 plants cauliflower cultivars Tropical Days, Exhibition, and Snow Queen; and chinese kale, were intercrossed |
| M2 | 93023-93052 | 30 plants |
| M3 | 93051-93080 | 30 plants 37 days |
|    | 93191-93217 | 27 plants |
|    | 93230-93252 | 23 plants |
| M4 | 92357-93280 | 24 plants 34 days |
| M5 | 93147-93452 | 36 plants 32 days |
| M6 | 93511-93534 | 24 plants 33 days |
| M7 | 93941-93960B | 24 plants 31 days |
| M8 | 149301-949320B | 24 plants 28 days |
| M9 | 149481-149500B | 24 plants 27 days | aSelection intensity 24/960 = 2.5%

As mentioned, stocks of rapid cycling Brassica CrGC-3 plants are maintained by the Crucifer Genetics Cooperative, 1630 Linden Drive, University of Wisconsin, Madison, Wis. 53706. The cooperative publishes a resource book describing the manipulation and handling of fast cycling Crucifer stock and also maintains seed reserves of the stocks. Seeds are readily available to anyone interested in Brassica botany or genetics by application for membership to the cooperative, which is open to all. Stocks of the plants are thus readily available and obtainable and maintained indefinitely by the cooperative.

The population designated CrGC-3, under the conditions described in Table 1, flowers with a mean time to flower of 30 days, is approximately 23 cm. tall to the first flower and produces approximately 20 seeds per plant. The seeds mature in 30 days. Thus the seed-to-seed cycle is 30 days. The stock is fully fertile with all other forms of *Brassica oleracea* and is now widely used by plant breeders and researchers in many applications of basic and applied science.

Development of Basic (dwarf) *Brassica oleracea* variety (BBC-1)

In order to develop a model plant that would have greater utility than the rapid cycling base population (CrGC-3) of the species *Brassica oleracea*, efforts were made towards the development of a shorter, more manageable plant type produced by Mendelian inheritance, within the CrGC-3 genetic background. Dwarf plants that would have substantially reduced internode length were developed so that the plants could grow more compactly under the fluorescent lamps of the illumination system of a standard research facility utilizing conditions similar to those described in Table 1. The initial object was thus to create smaller plants to economize on research laboratory space.

Seeds from a subset of rapid cycling CrGC-3 population (designated 171006) were exposed to 1.5% ethane methyl sulfonate (V:V), a potent mutagenic agent, under the following conditions. The seeds were presoaked in water for 2 hours at room temperature. After soaking, the water was poured off and the seeds covered with 1.5% aqueous ethane methyl sulfonate solution prepared just before use. The seeds were soaked with occasional shaking, for 6 hours at 20° C. The ethane methyl sulfonate solution was then poured off and neutralized by mixing with copious amounts of sodium bicarbonate in powder form. After 48-72 hours, the neutralized solution was flushed with excess water. The seeds were flushed with running water for 2 hours. The seeds were then sown and individual plants were grown. The progeny plants were self-pollinated to reveal potential recessive mutants in the second generation progeny. A schematic representation of the entire procedure is illustrated in FIG. 1 and described as follows. In FIG. 1, the plants are referred to by their six-digit serial numbers used in the procedure. The first generation of plants from the mutagenized seed is represented by sibling plants 180106 and 1810128, and their progeny by plants 180311 and 180326.

Selfed seeds of plant 180128 produced a dwarf-type plant with short internodes. However, the plant was weak and did not produce seed. Siblings of the dwarf, however, were expected to be carrying the dwarf mutation in the recessive condition at a frequency of ⅔. Sibling plant 180326, which appeared vigorous, was crossed with another vigorous plant 180311 derived from a separate plant 180106 of the mutagenized population. The $F_1$ plant from this cross was self-pollinated and the $F_2$ progeny yielded a single dwarf plant 207167.

Pollen from plants from the normal CrGC-3 population (149481-99) was crossed to the dwarf plant (207167) and 6 $F_1$ plants (207890) were derived from the cross. All $F_1$ plants appeared as normal CrGC-3 plants.

In the $F_2$ generation, of 167 plants grown, 36 plants were dwarf. The analyzed data above closely adheres to the hypothesis that the dwarf plant phenotype with extreme shortening of the internodes was conditioned by a single recessive gene designated by us dwfl/dwfl. Heterozygous plants are fully normal in phenotype to other CrGC-3 stocks and the plants expressing the recessive genotype are otherwise fully normal. Seeds of the dwarf stock were then mass increased as stock 214266. Plants grown from stock 214266 had many of the characteristics of the CrGC-3 stock with the exception that the plants had internodes shortened to 1–2 mm. compared with 30 mm. in normal CrGC-3 plants. Further, between 15 and 25 days after seeding, there was proliferation of the axillary shoots in the maturing plants giving rise to more than one flowering other respects, stock 214266 resembled CrGC-3 plants in leaves and flower size, days to flower, male and female fertility, and seed set (number of seeds per pod). This dwarfed form of *Brassica oleracea* CrGC-3 has been termed Basic *Brassica oleracea* or variety BBC-1. The C designates the genomic code for *Brassica oleracea* which distinguishes it from other basic Brassica stock or other Brassica species, e.g., Basic *Brassica campestris* is BBA and Basic *Brassica napus* is BBAC.

Description of BBC

Figure 2:
FIG. 2 is a perspective view of a typical dwarf plant of the variety *Brassica oleracea* BBC-1 in flower.
Figure 3:
FIG. 3 is a perspective view of a typical dwarf plant of the variety Brassica oleracea BBC-1 with seeds.

When grown under the standardized conditions (Table 1) for the rapid-cycling *Brassica oleracea* species, the BBC-1 plants emerge in 48–72 hours. Hypocotyl length is the same as for CrGC-3 or other forms of *Brassica oleracea*, and cotyledon expansion and size is normal. The first true leaf appears at about day 7, after which 5 or 6 more true leaves are produced. After 15 to 20 days, flower buds begin to appear. No elongation of the internodes occurs and the plant remains as a compact rosette of leaves. As the first flower buds reach approximately one-half cm. in length, the floral axis elongates slightly so that the flowers are produced just above the rosette formed by the leaves. As the first flowers open, the plant is between 25–30 days from seeding and is between 2 and 5 cm. from the cotyledonary node to the first flower on the axis. As flowers are produced, the floral axis elongates above the leaves to approximately 5–10 cm. Bud and flower sizes are normal. Flower parts such as sepals, petals, stamens, and pistils are all normal. Upon satisfactory pollination, abundant seeds, e.g., 10–20 seeds per pod, are set. At the time that flowering commences, buds in the axils of the 7–8 leaves develop into flowering shoots and also may produce flowers. A typical BBC-1 plant in flower is illustrated in FIG. 2. A typical BBC-1 plant with a good set of seeds is illustrated in FIG. 3. The flower colors in BBC represent the mix of white flowered types and light yellow flowered types found in CrGC-3. True breeding white or yellow flowered types can be readily extracted from the BBC-1. Apart from flower color, BBC-1 appears to the eye as a typical homogeneous variety plant typical of that illustrated in FIG. 2. The distinctive axillary branching pattern associated with the dwfl-gene in the CrGC-3 background greatly facilitates the vegetative cloning of individual plants through the rooting or cutting of the axillary shoots. A single plant can be "cloned" via cuttings in a period of one to two weeks.

The action of the dwfl gene is further characterized as producing dwarf plants that are insensitive to the internode extension hormone gibberellic acid GA). Most *Brassica oleracea* forms that grow in a tight rosette, such as cabbage and some kales, respond strongly by exhibiting internode elongation to the exogenous application of 100 to 1000 mg of GA per liter of water to their leaves. In contrast, plants bearing the dwfl gene and consequently exhibiting reduced internode spacing do not, thus distinguishing plants dwarfed as a consequence of the presence of this gene from those exhibiting short internode spacing for other reasons.

An important attribute of BBC-1 is its ability to grow, flower and produce seed under highly restricted rooting conditions. Although the growth pattern and phenotype described above relates to the standardized conditions of plant spacing and pot size given in Table 1, the BBC stock will grow satisfactorily in soil volume of 7 cubic centimeters at a plant density of 1,500 plants per meter square. Under these conditions plant size is reduced by about half of that under the standard conditions.

Linkage analysis of the dwfl allele is incomplete. Current data shows no linkage with the previously mapped chlorotic (pg2) or anthocyaninless (C-1) genes. Linkage data to known genes pg1, g11, g13, ms, Fn and Hrl is currently under investigation.

Of major importance from a research point of view, the plant of the present invention may be used as a repository for many genetic mutations of scientific, educational and potential economic interest. It is possible to genetically map a number of distinctive phenotypes by introducing single gene mutations into the dwarf plant. Examples of a few such mutations include color differences, presence or lack of hair on the plant, disease resistance, and morphological characteristics.

The rapid cycling, dwarf *Brassica oleracea* plant of new variety BBC-1 of the present invention also has a number of new potentially commercially interesting possibilities in the culinary and ornamental fields. Since the dwfl gene is a nuclear gene operating independently of most other genes in the plant, the gene will produce morphologically altered varieties of all the major cole crops (cabbage, cauliflower, broccoli, Brussel sprouts, kohlrabi, collards and the various kales) by relatively simple breeding programs to transfer the dwfl gene to the proper background. For example, it is possible to produce an edible miniature form of the various *Brassica oleracea* Chinese kale with the potential to be grown under extremely dense populations, i.e., up to 1,000 plants per square meter in less than 30 days. Additionally, due to the rapid flowering of the plant, it is possible that the rapid cycling dwarf plant of the present invention may have potential as an ornamental potted or bedding plant.

To facilitate practice of the present invention, a stock of seeds of *B. oleracea* var. BBC-1 has been deposited with the American Type Culture Collection (ATCC) on Oct. 1, 1987 and was accorded ATCC Accession No. 40376. These seeds will yield fully fertile and useful BBC-1 plants for variety study and maintenance and contain homozygously the dwfl gene for potential transfer to other Brassica varieties or species.

It may also be recognized from the foregoing description of the creation of the dwarf gene (dwfl) and the variety BBC-1, that the same mutagenesis and selection techniques may be used to create other dwarf mutant alleles in the fast-cycling *Brassica oleracea* population which may also be useful for plant breeding and research.

It is understood that the present invention is not limited to the particular embodiments illustrated herein but embraces all such modified forms thereof as come within the scope of the following claims.

What is claimed is:

1. Seed of *Brassica oleracea* comprising in its genome a homozygous allelic pair of dwarf (dwfl) genes from variety BBC-1 ATCC accession No. 40376 conditioning for reduced internode length, which seed will, upon cultivation, produce a fully fertile plant which is characterized by reduced internode length and which exhibits no increase in internode elongation upon the application of an aqueous solution having a concentration of 100 to 1000 mg gibberellic acid per liter of water.

2. Seed as claimed in claim 1 wherein the seed is of variety BBC-1, ATCC accession No. 40376.

3. Seed as claimed in claim 1 wherein the internode length of the resultant plants grown under standard conditions is about 1-2 mm.

4. Seed as claimed in claim 1 wherein the resultant plants will produce mature seed in about sixty days if grown under standard conditions.

5. Plants produced from the seed of claim 1.

6. Plants of *Brassica oleracea* comprising in their genome an allelic pair of dwarf (dwfl) genes derived from variety BBC-1 conditioning for reduced internode length, which is further characterized as exhibiting no increase in internode elongation upon application of an aqueous solution having a concentration of 100 to 1000 mg gibberellic acid per liter of water.

7. *Brassica oleracea* variety BBC-1, ATCC Accession No. 40376 and mutations and progeny thereof which contain in their genome an allelic pair of dwarf (dwfl) genes from BBC-1 which condition for dwarfism characterized by reduced internode length and which is further characterized by exhibiting no increase in internode elongation upon the application of an aqueous solution having a concentration of 100 to 1000 mg gibberellic acid per liter of water.

8. *Brassica oleracea* variety BBC-1, ATCC Accession No. 40376.

* * * * *